United States Patent [19]

Belter

[11] Patent Number: 5,777,185
[45] Date of Patent: Jul. 7, 1998

[54] PRODUCTION OF ORGANIC FLUORINE COMPOUNDS

[75] Inventor: Randolph K. Belter, Zachary, La.

[73] Assignee: LaRoche Industries Inc., Atlanta, Ga.

[21] Appl. No.: 925,999

[22] Filed: Sep. 9, 1997

[51] Int. Cl.$^6$ .................................................. C07C 17/08
[52] U.S. Cl. ............................................ 570/164; 570/165
[58] Field of Search ...................................... 570/164, 165

[56] References Cited

U.S. PATENT DOCUMENTS

| | | |
|---|---|---|
| 2,452,975 | 11/1948 | Whalley . |
| 3,836,479 | 9/1974 | Paucksch et al. . |
| 3,862,995 | 1/1975 | Martens et al. . |

*Primary Examiner*—Alan Siegel
*Attorney, Agent, or Firm*—Richard J. Hammond

[57] ABSTRACT

A process is disclosed for hydrofluorinating an olefinic hydrocarbon of the formula $$X-CX'=CX''-R'$$

where X, X' and X'' are the same or different and are hydrogen or halo and R' is hydrogen or $C_1$-$C_6$ alkyl, with hydrogen fluoride. The process is carried out by admixing the olefinic hydrocarbon with hydrogen fluoride in an imidofluoride hydrogen fluoride solvent having the formula $$R-(CF=NH_2)^+F^-\cdot\eta HF$$

where R is $C_1$ to $C_6$ alkyl, $C_1$ to $C_6$ alkyl substituted with halo or $C_6$ to $C_{10}$ aryl either unsubstituted or substituted with alkyl and $\eta$ is 0 or an integer that is at least 1.

13 Claims, No Drawings

PRODUCTION OF ORGANIC FLUORINE COMPOUNDS

FIELD OF INVENTION

This invention relates to the preparation of fluorinated hydrocarbons in the liquid phase using a liquid organic salt as solvent. More particularly, this invention relates to the preparation of a chlorofluoro aliphatic hydrocarbon by reacting an olefin or an olefinic halide with hydrofluoric acid in the presence of a liquid, organic salt solvent.

BACKGROUND OF THE INVENTION

The preparation of 1-chloro-1-fluoroethane can be carried out by the treatment of 1,1-dichloroethane with hydrofluoric acid in the presence of a Lewis acid catalyst. See for example in U.S. Pat. No. 2,452,975. While the desired chlorofluorocarbon is obtained in acceptable yields, this method has the distinct draw-back of using a relatively less readily available starting material. The process also disadvantageously produces stoichiometric quantities of hydrogen chloride. Further, relatively large amounts of spent catalyst result from this process which imposes additional costs for disposal in order to prevent environmental pollution.

A number of alternative methods for producing 1-chloro-1-fluoroethane use vinyl chloride as a reactant. This compound is more readily available than 1,1dichloroethane. The majority of these methods involve contacting vinyl chloride with hydrofluoric acid in the vapor phase in the presence of a catalyst. See, for example U.S. Pat. Nos. 3,862,995 and 3,836,479, and Belgium Patent No. 702,956. Unfortunately, the fluorination reaction is quite difficult to control and over-fluorination results in the substantial quantities of the undesired 1,1-difluoroethane being produced. Just as in the process using 1,1-dichloroethane, coking and disposal of the spent catalyst are also a problem.

Of the numerous liquid phase methods for the preparation of 1-chloro, 1-fluoroethane from vinyl chloride, European Patent 0 637 579 A1 is typical. This patent discloses a method which uses a Lewis acid catalyst in an organic solvent such as 1,1-dichloroethane to help decrease both over-fluorination and the formation of heavy halogenated by-products (tars). However, the economics of such a process are not favorable due to the disposal costs associated with the disposal of spent catalyst Additionally, these liquid phase processes consume solvent, which must be continuously replaced when running continuous operations. While the formation of tars is greatly decreased as compared to solvent free methodologies, an unacceptable quantity of vinyl chloride is lost as tars.

SUMMARY OF THE PRESENT INVENTION

According to the present invention, a process for the production of fluorinated aliphatic hydrocarbons, such as 1-chloro-1-fluoroethane comprises reacting an unsaturated olefinic hydrocarbon optionally containing a chloro group, such as vinyl chloride with anhydrous hydrogen fluoride in a solvent of an imidofluoride hydrofluoride liquid organic salt with no additional catalyst. This process does not use any catalyst. It therefore does not produce spent catalyst. Additionally, no observable tars are formed from this process, even after repeated recycles of solvent. Since the imidofluoride hydrofluoride solvent system is readily washed clean of any tars that may be inadvertently introduced (impurities, stabilizers, etc.) by using a hydrocarbon washing solvent, recycling the solvent is simple and provides an additional economic benefit.

DESCRIPTION OF THE PREFERRED EMBODIMENTS

The present invention relates to a process for hydrofluorinating an olefinic hydrocarbon of the formula

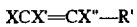

where X, X' and X" are the same or different and are hydrogen or halo and R' is hydrogen or $C_1$ to $C_6$ alkyl, with hydrogen fluoride. The process is carried out by admixing the olefinic hydrocarbon with hydrogen fluoride in an imidofluoride hydrogen fluoride solvent having the formula $$R\text{---}(CF\text{=}NH_2)^+F^-\cdot \eta HF$$

where R is hydrogen, $C_1$ to $C_6$ alkyl, $C_1$ to $C_6$ alkyl substituted with halo or $C_6$ to $C_{10}$ aryl either unsubstituted or substituted with alkyl and η is 0 or an integer that is at least 1.

The olefinic hydrocarbons of use in the present invention may be simple olefins such as where X, X' and X" are hydrogen, e.g., ethylene, propylene, 1- or 2-butene, 1- or 2-methylpropene-1 or 1- or 2-propene-2, etc. or such may be substituted with halogen, preferably chlorine such a vinyl chloride, 1- or 2-chloropropene-1, 1- or 2-chloro-1-methylpropene-1, etc.

As a preferred embodiment of the present invention, 1-chloro-1-fluoroethane is prepared by heating vinyl chloride with anhydrous hydrogen fluoride in an imidofluoride hydrofluoride solvent in a sealed reaction vessel.

The amide fluoride hydrofluoride solvent of use in the process according to the present invention can be prepared by the method of Wiechert, Heilmann and Mohr, Z. Chem., 3, 308 (1963). It has the general formula

where R is hydrogen, $C_1$ to $C_6$ alkyl, such a methyl, ethyl, n-propyl, isopropyl, n-butyl, n-pentyl, n-hexyl, etc.; $C_1$ to $C_6$ alkyl substituted with halo, such as trichloromethyl, dichloromethyl, chloromethyl, etc., or $C_6$ to $C_{10}$ aryl either unsubstituted or substituted with alkyl, such as phenyl, 4-methylphenyl, naphthyl, etc. and η is 0 or an integer that is at least 1, such as 2, 3, 4, etc. Preferably, n is 1 thru 4. Most preferably n is 1.

The amount of imidofluoride hydrofluoride solvent used in the process of the present invention is typically equimolar to the molar amount of olefinic hydrocarbon. However, more than or less than this equimolar amount can be used, such as a ratio of solvent to olefinic hydrocarbon of from about 0.1 to about 10.0 of solvent to 1.0 of olefinic hydrocarbon. Preferably the ratio of olefinic hydrocarbon to solvent is from about 0.5 to about 5.0 of solvent to 1.0 of olefinic hydrocarbon.

While not wishing to be bound by the following, at temperatures of about 80° to 100° C., it is believed that approximately one mole of hydrogen fluoride is available for reaction with the olefinic hydrocarbon. The remainder remains sequestered presumably as a higher-order complex (i.e., $R\text{---}(CF\text{=}NH_2)^+F^-\cdot\eta 5HF$). At higher temperatures, more hydrogen fluoride becomes available for reaction. Conversely, at lower temperatures, less hydrogen fluoride is available. Accordingly, the amount of hydrogen fluoride available for reactivity varies with the temperature of the reaction.

The preferred amount of hydrogen fluoride used in the process of the present invention is about six moles of hydrogen fluoride per mole of imidofluoride hydrofluoride solvent. However, greater than four and most preferably greater than six moles of hydrogen fluoride are used per mole of imidofluoride hydrofluoride solvent. Amounts of imidofluoride hydrofluoride solvent in amounts of greater then 10 moles are not advantageous.

The temperature at which the reaction is carried out may vary between about 50° C. to about 150° C., preferably greater than 60° C. and most preferably greater than 80° C.

Where the olefinic hydrocarbon is vinyl chloride, the reaction product is 1-chloro-1-fluoroethane, which is collected from the reaction vessel as a gas, leaving the higher-order imidofluoride hydrofluoride·6HF complex behind. The complex may be used "as is" for recharging with hydrogen fluoride and vinyl chloride for repeated batch preparations of 1-chloro-1-fluoroethane. The complex, as a liquid, is also suitable for continuous flow operations.

No visible tar formation occurs in the reaction of the olefinic hydrocarbon with hydrogen fluoride in the imidofluoride hydrofluoride·6HF complex solvent. However, tar may accumulate from the recycle of the solvent. The actual content of the tar may be quantified conveniently, by extracting such tar from the imidofluoride hydrofluoride solvent by using a hydrocarbon solvent, e.g., hexane, petroleum ether, etc. This technique is additionally advantageous since the imidofluoride hydrofluoride solvent is not altered by the extraction. Thus, any accumulated tars may be removed by means of extraction and the imidofluoride hydrofluoride solvent returned to service. This process is also useful in continuous flow operations, thereby obviating the need for waste solvent controls (disposal, refining, etc.).

When using vinyl chloride as the olefinic hydrocarbon, and modifying the reaction conditions, 1,1-difluoroethane may be the desired product, rather than 1-chloro-1-fluoroethane.

Specifically, if a Lewis acid were used, i.e., tin tetrachloride, in catalytic or stoichiometric amounts, 1,1-difluoroethane is produced using the imidofluoride hydrofluoride solvent. Similarly, 1,1-difluoroethane may be produced from 1-chloro-1-fluoroethane in this same manner. A co-solvent, i.e., 1,1-dichloroethane, has been found to be preferable in this latter reaction.

The following examples are for the purpose of illustration only and are in no to be regarded as limiting.

EXAMPLE 1

The preparation of imido fluoride hydrofluoride solvent ($R=CH_3$)

An evacuated 300 ml autoclave was charged with 41 g (1.0 mole) of acetonitrile. The autoclave was cooled with a dry ice/acetone bath and 80 g (4.0 moles) of anhydrous. Hydrofluoric acid was slowly added. The reactor was heated to 100° C. for one hour. The pressure of the reactor was observed to decrease from 90 psi to 70 psi. The reactor was cooled and the $CH_3-(CF=NH_2)^+F^-\cdot 2HF$ solvent used as is.

EXAMPLE 2

The preparation of 1chloro-1-fluoroethane from vinyl chloride (solvent $R=CH_3$)

A 300 ml autoclave was charged with 81 g of $CH_3-(CF=NH_2)^+F^-\cdot 2HF$ (1.0 mole). The reactor was evacuated and cooled with a dry ice/acetone bath. 140 g (7.0 moles) of anhydrous HF was charged, followed by 50 g (0.5 moles) of vinyl chloride. The reactor was heated to 100° C. for a period of 2 to 3 hours. The reactor was cooled to 30° C. and the product gases vented through a caustic scrubber into a cold trap. The recovery of products was quantitative with a composition of 87.6% 1-chloro, 1-fluoroethane, 7.6% 1,1-difluoroethane, 3.8% vinyl chloride and 1.0% 1, 1 -dichloroethane.

The total weight of remaining catalyst was determined and anhydrous. HF charged to replace that amount lost to the product recovery procedure. A second charge of vinyl chloride was put into the reactor and a second reaction initiated. A total of nine consecutive runs were performed in this manner. After the ninth reaction, the imido fluoride hydrofluoride solvent was extracted with hexane. The hexane extract was evaporated to dryness and the weight of residue determined. No residue (tar) was observed.

EXAMPLE 3

The preparation of 1chloro-1-fluoroethane from vinyl chloride (solvent $R=Ph$)

A 300 ml autoclave was charged with 72 g of $Ph-(CF=NH_2)^+F^-\cdot 2HF$ (0.5 mole). The reactor was evacuated and cooled with a dry ice/acetone bath. 100 g (5.0 moles) of anhydrous HF was charged, followed by 53 g (0.85 moles) of vinyl chloride. The reactor was heated to 100° C. for 15 minutes. The reactor was cooled to 30° C. and the product gases vented through a caustic scrubber into a cold trap. The recovery of products was quantitative with a composition of 85% 1-chloro, 1-fluoroethane, 6.7% 1,1-difluoroethane, 8.2% vinyl chloride and <1% 1,1-dichloroethane. No tar residue was observed.

EXAMPLE 4

The preparation of 1,1-dichloro-1-fluoroethane from vinylidene chloride

A 300 ml autoclave was charged with 81 g of $CH_3-(CF=NH_2)^+F^-\cdot 2HF$ (1.0 mole). The reactor was evacuated and cooled with a dry ice/acetone bath. 100 g (5.0 moles) of anhydrous HF was charged, followed by 73.5 g (0.5 moles) of vinylidene chloride. The reactor was heated to 50° C. for a period of 2 hours. The reactor was cooled to 20° C. and the product and the product isolated by liquid phase separation as the more dense layer. The recovery of products was quantitative with a composition of 86.9% 1,1 -dichloro, 1-fluoroethane, 6.4% 1-chloro-1,1-difluoroethane, and 6.7%% vinylidene chloride.

The total weight of remaining catalyst was determined and anhydrous. HF charged to replace that amount lost to the product recovery procedure. A second charge of vinyl chloride was put into the reactor and a second reaction initiated. A total of three consecutive runs were performed in this manner. After the third reaction, the imido fluoride hydrofluoride solvent was extracted with hexane. The hexane extract was evaporated to dryness and the weight of residue determined. No residue (tar) was observed.

EXAMPLE 5

The preparation of 1,1-difluoroethane from vinyl chloride

A 450 ml autoclave was charged with 27 g of $CH_3-(CF=NH_2)^+F^-\cdot 2HF$ (1.0 mole). The reactor was evacuated and cooled with a dry ice/acetone bath. 92 g (4.6 moles) of anhydrous HF was charged, followed by 43 g (0.17 moles) of tin tetrachloride. The reactor was heated to 70° C. for 1 hour. The reactor was again cooled with dry ice. 66 g (0.66 mol) of 1,1-dichloroethane was charged followed by 62 g (1.0 mol) of vinyl chloride. The reactor was heated to 70° C. for 2 hours. The reactor was then cooled to room temperature and the product gases vented through a caustic scrubber into a cold trap. Analysis of the product showed a composition of 85.5% 1,1-difluoroethane, 7.9% 1-chloro, 1-fluoroethane, 0% vinyl chloride and 6.6% 1,1-dichloroethane.

I claim:

1. A process for hydrofluorinating an olefinic hydrocarbon of the formula

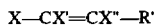

$$X-CX'=CX''-R'$$

where X, X' and X" are the same or different and are hydrogen or halo and R' is hydrogen or $C_1$ to $C_6$ alkyl, with hydrogen fluoride, wherein said process is carried out by admixing the olefinic hydrocarbon with hydrogen fluoride in an imidofluoride hydrogen fluoride solvent having the formula

$$R-(CF=NJ_2)^+F^-\cdot\eta HF$$

where R is hydrogen, $C_1$ to $C_6$ alkyl, $C_1$ to $C_6$ alkyl substituted with halo or $C_6$ to $C_{10}$ aryl either unsubstituted or substituted with alkyl and $\eta$ is 0 or an integer that is at least 1.

2. The process according to claim 1 wherein X is chloro and X' and X" are hydrogen.

3. The process according to claim 2 wherein R' is hydrogen.

4. The process according to claim 3 wherein R is selected from the group consisting of methyl, ethyl, propyl, isopropyl and n-butyl and n is 1.

5. The process according to claim 3 wherein R is selected from the group consisting of phenyl, naphthyl and 4-methylphenyl and n is 1.

6. The process according to claim 3 wherein R is selected from the group consisting of $C_1$ to $C_6$ alkyl substituted with halo and n is 1.

7. The process according to claim 4 wherein from about 0.1 to about 10.0 moles of solvent is used for each mole of olefinic hydrocarbon.

8. The process according to claim 5 wherein from about 0.1 to about 10.0 moles of solvent is used for each mole of olefinic hydrocarbon.

9. The process according to claim 6 wherein from about 0.1 to about 10.0 moles of solvent is used for each mole of olefinic hydrocarbon.

10. The process according to claim 7 wherein about 1.0 mole of solvent is used for each mole of olefinic hydrocarbon.

11. The process according to claim 8 wherein about 1.0 mole of solvent is used for each mole of olefinic hydrocarbon.

12. The process according to claim 9 wherein about 1.0 mole of solvent is used for each mole of olefinic hydrocarbon.

13. A process for hydrofluorinating an olefinic hydrocarbon of the formula

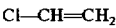

$$Cl-CH=CH_2$$

with hydrogen fluoride, wherein said process is carried out by admixing the olefinic hydrocarbon with hydrogen fluoride in an imidofluoride hydrogen fluoride solvent having the formula

$$R-(CF=NH_2)^+F^-\cdot\eta HG$$

where R is $C_1$ to $C_6$ alkyl, $C_1$ to $C_6$ alkyl substituted with halo or $C_6$ to $C_{10}$ aryl either unsubstituted or substituted with alkyl and $\eta$ is 0 or an integer that is at least 1.

* * * * *

UNITED STATES PATENT AND TRADEMARK OFFICE
CERTIFICATE OF CORRECTION

PATENT NO. : 5,777,185
DATED     : July 7, 1998
INVENTOR(S) : Randolph K. Belter It is certified that error appears in the above-identified patent and that said Letters Patent is hereby corrected as shown below:

Column 2, lines 46 and 47, the letter "n" in each instance should read -- $\eta$ --.

Column 2, line 62, the formula reading "R-(CF=NH$_2$)$^+$ F$^-$ · $\eta$5HF" should read -- R-(CF=NH$_2$)$^+$ F$^-$ · 5HF --. Column 3, line 15 and line 22, the term "·6HF" should read -- ·5HF --. Claim 1, the second formula reading "R-(CF=NJ$_2$)$^+$ · $\eta$HF" should read -- R-(CF=NH$_2$)$^+$ · $\eta$HF --. Claim 4, line 3, Claim 5, line 3 and Claim 6, line 3, in each Claim, the letter "n" should read -- $\eta$ --. Claim 13, the second formula reading "R-(CF=NH$_2$)$^+$ F$^-$ · $\eta$HG" should read -- R-(CF=NH$_2$)$^+$ F$^-$ · $\eta$HF --

Signed and Sealed this

Twelfth Day of January, 1999

*Attest:*

*Attesting Officer*        *Acting Commissioner of Patents and Trademarks*